(12) United States Patent
Frerichs

(10) Patent No.: US 8,621,923 B2
(45) Date of Patent: Jan. 7, 2014

(54) HUMIDITY SENSOR

(75) Inventor: Heinz-Peter Frerichs, St. Peter (DE)

(73) Assignee: Micronas GmbH, Freiburg i. Br. (DE)

( * ) Notice: Subject to any disclaimer, the term of this patent is extended or adjusted under 35 U.S.C. 154(b) by 505 days.

(21) Appl. No.: 12/908,979

(22) Filed: Oct. 21, 2010

(65) Prior Publication Data

US 2011/0088466 A1    Apr. 21, 2011

(30) Foreign Application Priority Data

Oct. 21, 2009   (EP) .................................. 09013311

(51) Int. Cl.
*G01N 27/12*   (2006.01)

(52) U.S. Cl.
USPC ...................... 73/335.02; 73/29.05

(58) Field of Classification Search
USPC ........................... 73/335.02, 29.05
See application file for complete search history.

(56) References Cited

U.S. PATENT DOCUMENTS

| | | | |
|---|---|---|---|
| 4,423,371 A | | 12/1983 | Senturia et al. |
| 4,920,451 A | * | 4/1990 | Sakai et al. .................... 361/286 |
| 6,615,659 B2 | * | 9/2003 | Shibue et al. ............... 73/335.02 |
| 8,291,745 B2 | * | 10/2012 | Karabacak et al. .......... 73/24.01 |
| 2004/0194534 A1 | * | 10/2004 | Porter et al. .................. 73/24.01 |
| 2009/0078026 A1 | * | 3/2009 | Wilbertz et al. ............. 73/31.06 |
| 2009/0246084 A1 | * | 10/2009 | Wilbertz et al. ................ 422/98 |
| 2010/0176826 A1 | | 7/2010 | Lehmann et al. |

FOREIGN PATENT DOCUMENTS

| | | | | |
|---|---|---|---|---|
| CN | 1445538 A | 10/2003 | | |
| EP | 1 176 418 A2 | 1/2002 | | |
| JP | 1-124755 | * | 5/1989 | .................. 73/29.05 |
| JP | 3-137555 | * | 6/1991 | .................. 73/29.05 |
| WO | WO 2008/122390 A1 | 10/2008 | | |

OTHER PUBLICATIONS

Marquardt G: "Feuchtigkeitsempfindliche Feldeffekttransistoren" Wissenschaftlichezeitschrift der Technischen Hochschule Karl-Marx Stadt, Technische Universitaet Chemnitz, DE, Bd. 25, Nr. 6, Jan. 1, 1983, Seiten 884-887, XP009131757 ISSN: 0372-7610.
Lee S P et al: "Humidity sensitive field effect transistors" Sensors and Actuators B, Elsevier Sequoia S.A., Lausanne, CH, Bd. 35, Nr. 1, Sep. 1, 1996, Seiten 80-84, XP004049735 ISSN: 0925-4005 DOI: 10. 1016/S0925-4005 (96) 02018-7.

\* cited by examiner

*Primary Examiner* — Daniel S Larkin
(74) *Attorney, Agent, or Firm* — Muncy, Geissler, Olds & Lowe, PLLC

(57) ABSTRACT

A humidity sensor has, on a substrate, at least one voltage sensor with a sensor region and at least one control electrode. The control electrode is connected to a signal source which is designed such that a variable control voltage can be applied to the control electrode. A moisture-permeable sensor layer whose dielectric constant depends on humidity is located on the sensor region. The control electrode is adjacent to the sensor layer in such a manner that the measured voltage signal of the voltage sensor depends on the control voltage and the humidity. The voltage sensor is connected to an analysis unit for ascertaining the humidity on the basis of the measured voltage signal. In the vertical projection onto the plane in which the substrate extends, the control electrode is located laterally next to the sensor region.

9 Claims, 4 Drawing Sheets

HUMIDITY SENSOR

This nonprovisional application claims priority under 35 U.S.C. §119(a) to European Patent Application No. EP 09013311.7, which was filed on Oct. 21, 2009, and which is herein incorporated by reference.

BACKGROUND OF THE INVENTION

1. Field of the Invention

The invention relates to a humidity sensor which has, on a substrate, at least one voltage sensor with a sensor region and at least one control electrode that is connected to a signal source designed such that a variable control voltage can be applied to the control electrode, wherein a moisture-permeable sensor layer whose dielectric constant depends on humidity is located on the sensor region adjacent to the control electrode, wherein the control electrode is adjacent to the sensor layer in such a manner that the measured voltage signal of the voltage sensor depends on the control voltage and the humidity, and wherein the voltage sensor is connected to an analysis unit for ascertaining the humidity on the basis of the measured voltage signal.

2. Description of the Background Art

A humidity sensor of this nature is known from EP 1 176 418 A2. The humidity sensor has a semiconductor chip in which a field-effect transistor is integrated as the voltage sensor. In a semiconductor substrate, the field-effect transistor has a drain and a source between which a channel region is formed as a voltage-sensitive sensor region. Located on the channel region is a gas-sensitive sensor layer that is polarizable independently of the humidity and whose dielectric constant depends on the humidity. The sensor layer is made of a porous, gas-permeable material. Located on the sensor is a control electrode, which likewise is porous and gas-permeable and completely covers both the sensor layer and a passivation layer that is laterally contiguous therewith. To measure the humidity, a voltage is first applied to the control electrode in order to determine the humidity-dependent change in the relative dielectric constant. The humidity is then ascertained using the measured change. The humidity sensor has the disadvantage that an additional fabrication step is required during its fabrication, after the application of the sensor layer on the channel region, in which a porous metallization is applied as the control electrode to the sensor layer and the passivation layer laterally contiguous therewith. The metallization must adhere to the sensor layer and the passivation layer. This results in certain restrictions in the choice of materials for the metallization and the sensor layer. It is also unfavorable that only porous, gas-permeable layers can be used as metallization.

SUMMARY OF THE INVENTION

In is therefore an object of the invention to provide a humidity sensor of the initially mentioned type that can be manufactured economically.

Thus, in a vertical projection onto the plane in which the substrate extends, the control electrode is located laterally next to the sensor layer and/or beneath the sensor layer between it and the substrate, without covering the sensor layer. As an advantageous result, during fabrication of the humidity sensor no additional layer needs to be applied to the sensor layer after the sensor layer has been applied. The sensor layer can thus be designed as a cover layer that stands in direct contact with the atmosphere surrounding the humidity sensor. Consequently, the control electrode can be made of a material that is impermeable, or only poorly permeable, to moisture. Nevertheless, the humidity sensor according to the invention permits a rapid response of the humidity measurement signal to a change in the humidity.

The control electrode can surround the sensor region in the form of a ring. By this means, the variable control voltage or the variable voltage can act on the sensor layer in a better and more homogeneous fashion, for example in that dipoles located in the sensor region are aligned by the voltage change or are induced by charge displacement. This charge displacement, which also is dependent on the humidity, can be capacitively detected by means of the voltage sensor.

In an embodiment of the invention, the sensor layer completely covers the control electrode. The measured voltage signal of the voltage sensor is then largely insensitive to contaminants occurring at the humidity sensor. Such contaminants are difficult to avoid, especially after the humidity sensor has been in service for a relatively long time. Moreover, the humidity sensor can then be manufactured more easily and more economically.

An electrically insulating layer can be located between the control electrode and the sensor layer. The thickness of the insulating layer or the spacing between the control electrode and the sensor layer is chosen here such that the electric field created by the control voltage acts capacitively on the sensor layer through the insulating layer. The sensor layer, in turn, is capacitively coupled to the sensor region of the voltage sensor. As a result of the insulating layer, the measured voltage signal is still less sensitive to contamination on the humidity sensor. The insulating layer can be a native insulating layer, which is produced by contact of the control electrode with atmospheric oxygen during fabrication of the humidity sensor.

In an embodiment of the invention, the sensor layer can be made of polymethyl methacrylate (PMMA) or contains polymethyl methacrylate (PMMA). The humidity sensor then permits particularly high measurement sensitivity.

The voltage sensor can be a field-effect transistor that has a semiconductor substrate of a first charge carrier type on which are located a drain and a source of a second charge carrier type, and when a channel region that forms the sensor region is provided between drain and source. The variable voltage can be measured in a high-resistance manner using the field-effect transistor. The channel region of the field-effect transistor is preferably located directly beneath the sensor layer, thereby allowing measurement signal extraction that is largely insensitive to EMC influences and also allowing the sensor to have compact dimensions.

In another embodiment of the invention, the sensor region is comprised of a preferably planar measurement electrode, which is connected by a conductive trace to the gate electrode of a field-effect transistor and/or an input of a high-resistance instrumentation amplifier. Thus, the channel region of the field-effect transistor or the instrumentation amplifier can also be located laterally next to the sensor region.

In an embodiment, the signal source is designed such that it can generate a control voltage with at least one jump, in particular a square-wave voltage. The voltage measurement signal of the voltage sensor can then be analyzed in a simple manner in the analysis unit. However, the invention is not restricted to the use of a control voltage that has a jump. In principle, the invention can also have an arbitrary signal shape deviating from a DC signal. In the analysis unit, the effect that the signal shape of the control voltage has on the voltage measurement signal must then be appropriately calculated out of the voltage measurement signal, for example by correlation of the voltage measurement signal with the control voltage.

The signal source and the analysis unit can be integrated in the substrate. The humidity sensor is then still more economical to produce, and in addition allows very compact dimensions.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
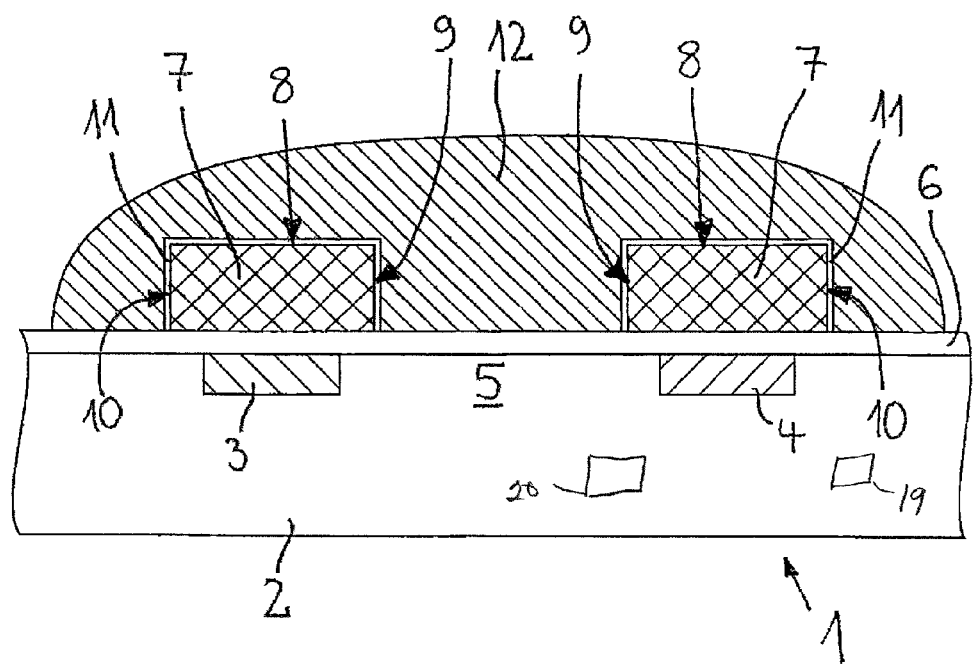
FIG. 1 shows a cross-section through a first exemplary embodiment of a humidity sensor.

A humidity sensor has a semiconductor chip 1, which has a substrate 2 of a first charge carrier type. Integrated into the substrate 2 is a voltage sensor that is designed as a field-effect transistor. As is evident from FIG. 1, the voltage sensor has a drain 3 and a source 4 of a second charge carrier type, which are set into the substrate 2 as wells. Located between the drain 3 and the source 4 is a channel region, which serves as the sensor region 5 for measuring a voltage change. Located on the substrate 2 is an electrically insulating layer 6, which extends continuously over the drain 3, the source 4, and the sensor region 5, except for places where electrical contact terminals are located. The insulating layer 6 can be an oxide layer, for example.

Figure 2:
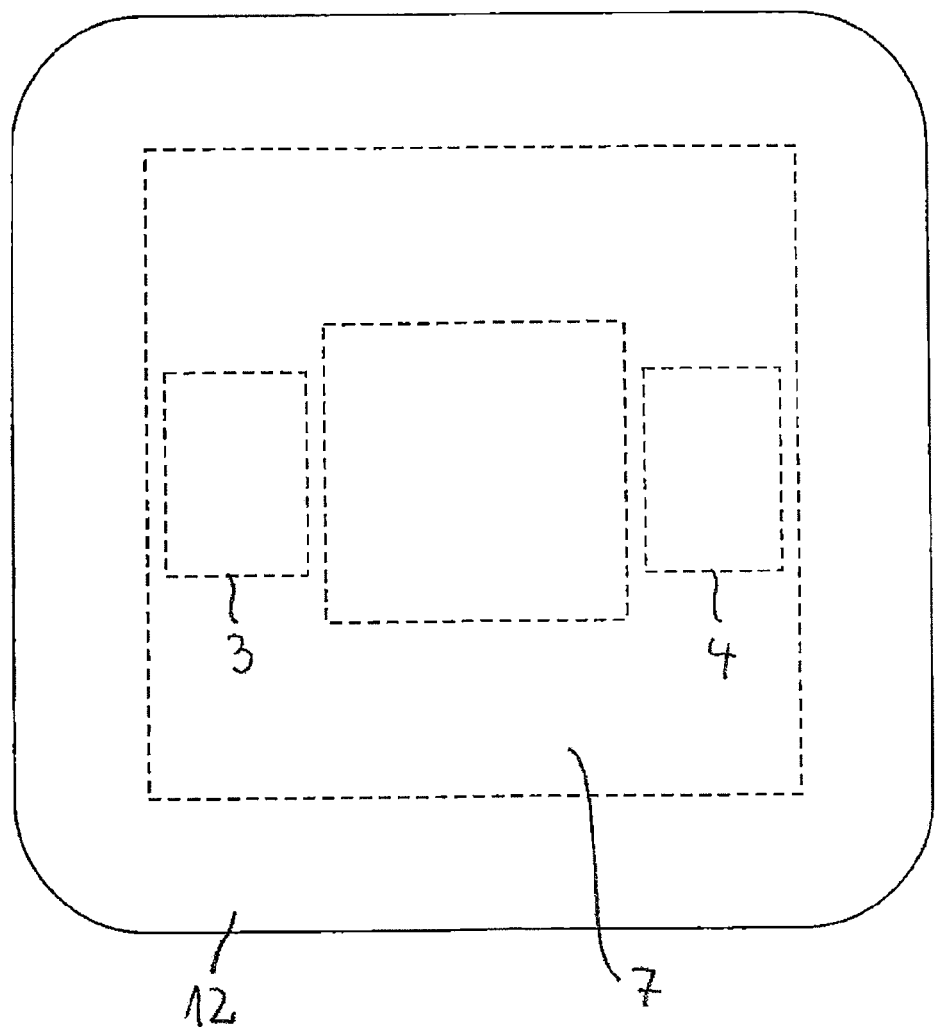
FIG. 2 shows a top view of the humidity sensor.

A control electrode 7 made of an electrically conductive material is provided on the insulating layer 6; in the top view shown in FIG. 2 of the plane in which the substrate 2 extends, this control electrode is located laterally next to the sensor region 5. It is clearly visible that the control electrode 7 is designed as an annular electrode that surrounds the sensor region 5. The control electrode 7 is coated on its surface 8 facing away from the substrate 2 and on its inner circumferential surface 9 and its outer circumferential surface 10 with an electrically insulating layer 11, which can be a native oxide layer, for example.

Located on the insulating layer 6 above the sensor region 5 is a humidity-permeable sensor layer 12 whose dielectric constant is a function of humidity. The sensor layer 12 is preferably made of polymethyl methacrylate.

The sensor layer 12 extends unbroken over the first surface region of the insulating layer 6 surrounded by the control electrode 7, over the control electrode 7, and over an approximately ring-shaped second surface region of the insulating layer 6 that surrounds the outside of the control electrode. It is evident in FIG. 1 that the control electrode 7 is completely covered on its surface 8 facing away from the substrate 2 and on its inner circumferential surface 9 and its outer circumferential surface 10 by the sensor layer 12. Here, the control electrode 7 is electrically insulated from the sensor layer 12 by the insulating layer 11.

The control electrode 7 is connected to a signal source 19 by a conductive trace integrated into the semiconductor chip 1. Using the signal source 19, a variable control voltage, preferably a square-wave signal with predetermined frequency and predetermined amplitude, can be applied between the substrate 2 and the control electrode 7. The control electrode 7 is adjacent to the sensor layer 12 in such a manner that the electric field created by the control voltage extends through the insulating layer 11 into the sensor layer 12 and polarizes charge carriers therein.

Figure 3:
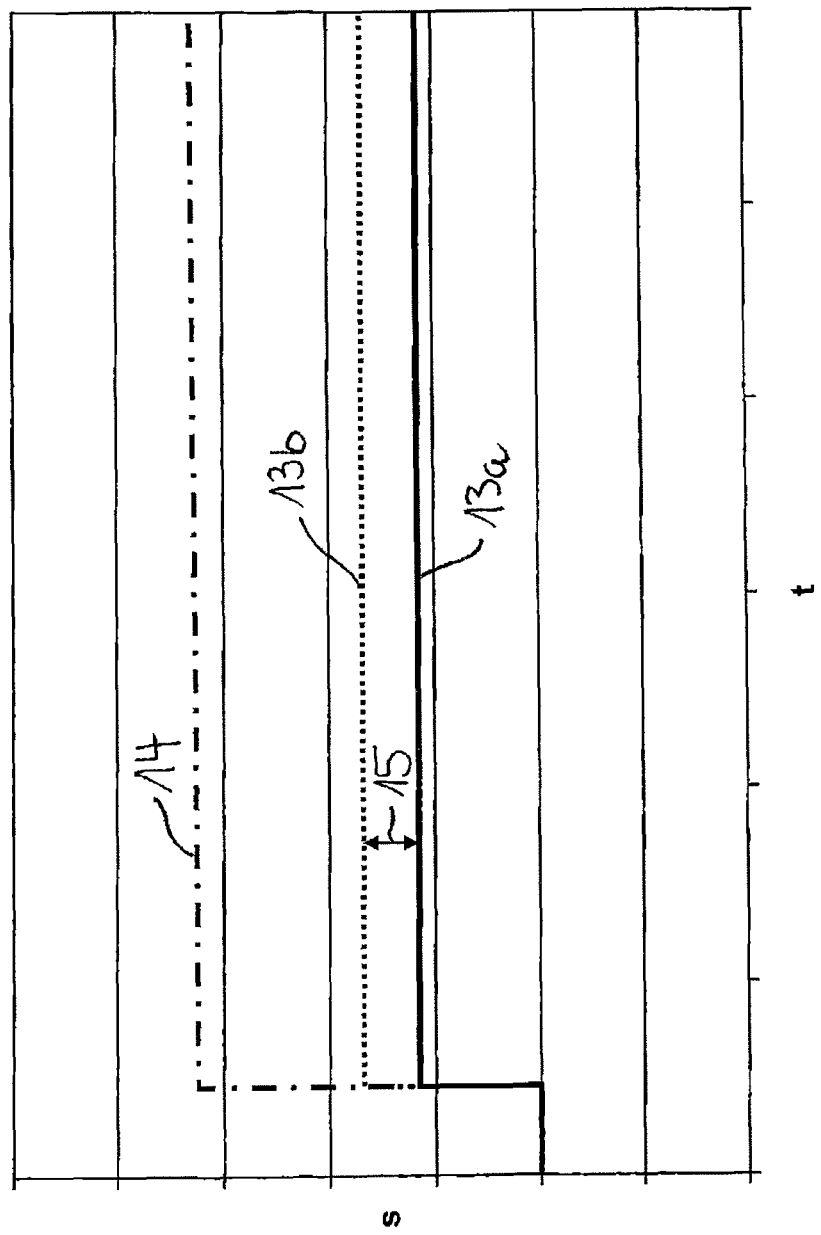
FIG. 3 shows a graphical representation of two voltage measurement signals of the humidity sensor plotted for different relative humidities, during the application of a control voltage to a control electrode, where the time t is represented on the abscissa and the voltage measurement signal s or the control voltage is represented on the ordinate.

Using the voltage sensor, this polarization, which depends on the control voltage and the humidity, is measured capacitively in the form of a measured voltage signal 13a, 13b (FIG. 3). In order to determine the humidity using the measured voltage signal 13a, 13b, the voltage sensor is connected to an analysis unit 20. This analysis unit 20 may be integrated in the semiconductor chip 1.

It can be seen in FIG. 3 that after the occurrence of a jump in the control voltage, the measured voltage signal 13a, 13b also has a corresponding jump. It can also be seen that with a constant shape 14 of the control voltage, the measured voltage signal 13a, 13b is shifted by an offset 15 when the relative humidity changes. With an increase in the humidity, the value of the measured voltage signal 13a, 13b increases, and with a decrease in the humidity, the value of the measured voltage signal 13a, 13b decreases.

Reference values for the offset 15 are prepared as a function of the relative humidity, for example in the form of characteristic curves or in the form of a family of curves for which sampling points are stored. The relative humidity can then be determined using the measured voltage signal 13a, 13b and the reference values, for example in order to generate an analog signal proportional to the relative humidity and/or a corresponding digital signal in the analysis unit.

Figure 4:
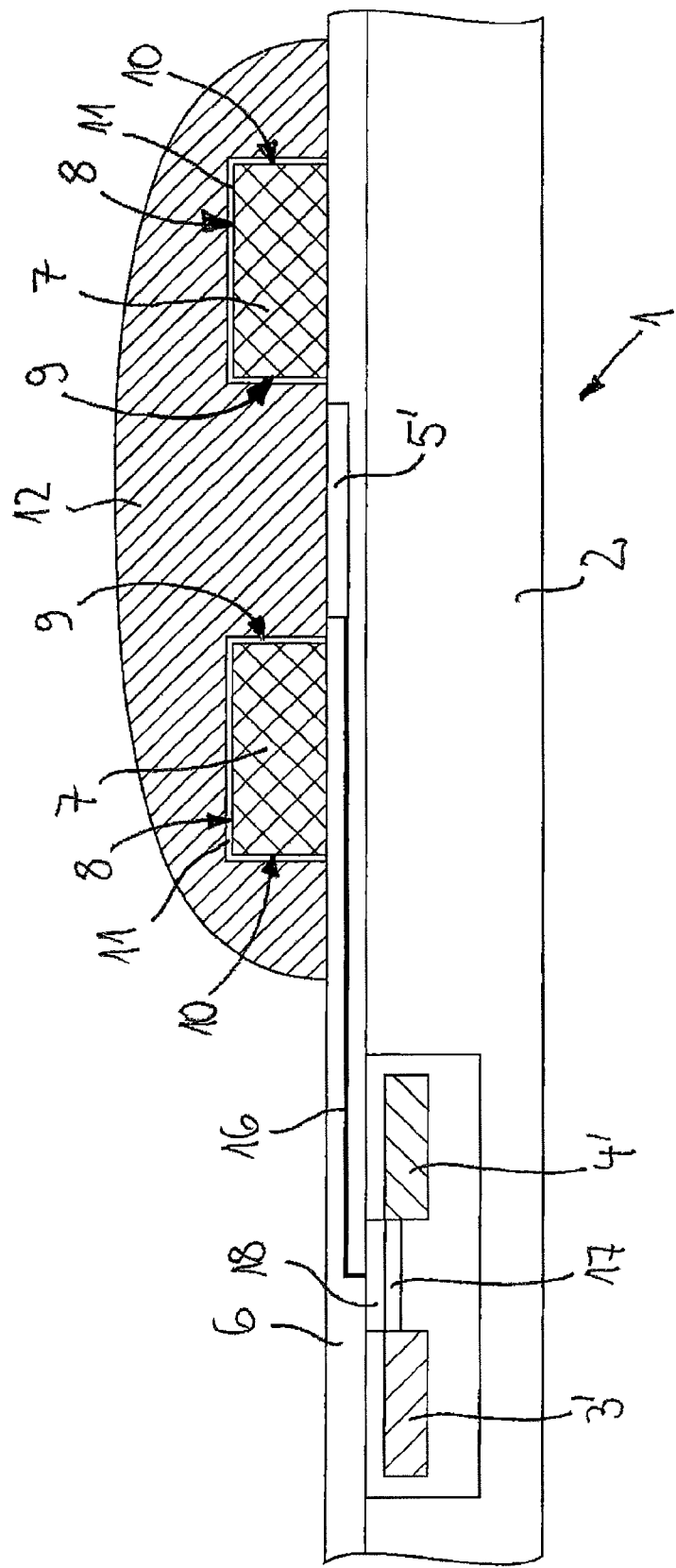
FIG. 4 shows a cross-section through a second exemplary embodiment of the humidity sensor.

In the exemplary embodiment shown in FIG. 4, the sensor region 5' is composed of a planar measurement electrode that is located beneath the sensor layer 12 at a distance from the control electrode 7 and is connected by a conductive trace 16 to a gate electrode 18 that is located over a channel region 17 of a field-effect transistor placed between a drain 3' and a source 4'. It is clearly visible that the field-effect transistor is integrated into the substrate 2 of the semiconductor chip 1 laterally next to the arrangement comprising the sensor region 5', the control electrode 7, the insulating layer 11 and the sensor layer 12.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:
1. A humidity sensor comprising:
   at least one voltage sensor with a sensor region;
   at least one control electrode configured to receive a variable control voltage, the voltage sensor and the control electrode being arranged on a substrate; and a moisture-permeable sensor layer whose dielectric constant depends on humidity is arranged on the sensor region, wherein the control electrode is adjacent to the sensor layer such that the measured voltage signal of the voltage sensor depends on a control voltage and the humidity, wherein the measured voltage signal is a function of the humidity, wherein said moisture-permeable sensor layer completely surrounds and covers portions of the control electrode above said sensor layer, and wherein, in a vertical projection onto a plane in which the substrate extends, the control electrode is located laterally next to the sensor region.

2. The humidity sensor according to claim 1, wherein the control electrode surrounds the sensor region in the form of a ring.

3. The humidity sensor according to claim 1, wherein an electrically insulating layer is arranged between the control electrode and the sensor layer.

4. The humidity sensor according to claim 1, wherein the sensor layer is made of polymethyl methacrylate or contains polymethyl methacrylate.

5. The humidity sensor according to claim 1, wherein the voltage sensor is a field-effect transistor that has a semiconductor substrate of a first charge carrier type on which are located a drain and a source of a second charge carrier type, and wherein a channel region that forms the sensor region is provided between the drain and the source.

6. The humidity sensor according to claim 1, wherein the sensor region is comprised of a planar measurement electrode, which is connected by a conductive trace to a gate electrode of a field-effect transistor or is configured to be connected to an input of a high-resistance instrumentation amplifier.

7. The humidity sensor according to claim 1, wherein the the variable control voltage is a square-wave voltage.

8. The humidity sensor according to claim 1, wherein the variable control voltage is generated by a signal source and the humidity is determined from said measured voltage signal by an analysis unit.

9. The humidity sensor according to claim 8, wherein the signal source and the analysis unit are integrated in the substrate.

* * * * *